United States Patent [19]

Plumpe, Jr.

[11] 3,959,108
[45] May 25, 1976

[54] SYSTEM FOR AUTOMATICALLY MEASURING AND CONTROLLING THE SULFATE CONTENT OF A CHROMIUM PLATING SOLUTION

[76] Inventor: William H. Plumpe, Jr., 11109 Conway Road, St. Louis, Mo. 63131

[22] Filed: May 1, 1974

[21] Appl. No.: 465,806

Related U.S. Application Data

[63] Continuation of Ser. No. 212,198, Dec. 27, 1971, abandoned.

[52] U.S. Cl. .............................. 204/195 R; 204/1 T; 137/93
[51] Int. Cl.² ...................................... G01N 27/46
[58] Field of Search ........ 204/195 R, 195 C, 195 H,

[56] References Cited
UNITED STATES PATENTS

| | | | |
|---|---|---|---|
| 3,235,477 | 2/1966 | Keyser et al. | 204/195 P |
| 3,661,751 | 5/1972 | Wilson | 204/195 C |
| 3,716,460 | 2/1973 | Weisstuch et al. | 204/195 C |

OTHER PUBLICATIONS

Lingane, "Electroanalytical Chemistry," 2d Ed. Rev. & Enlarged, Interscience Publishers, Inc. N. Y. 1958, p. 247.
Booth et al., "Talanta," 1970, Vol. 17, No. 11, pp. 1059–1065.

*Primary Examiner*—T. Tung

[57] ABSTRACT

This invention relates to a system for automatically measuring and controlling the sulfate content of a chromium plating solution including sulfuric acid and chromium trioxide in water, the measuring system including means for automatically applying a constantly increasing voltage across the electrodes of a probe immersed in the solution, and for detecting the peak current flow through the solution between the electrodes, which peak amplitude is directly proportional to the percent sulfate in the solution. The electrodes are especially designed to produce accurate readings and are of materials that are noncorrosive in the plating solution. The system further includes a recording device for recording the percent sulfate in solution in response to the peak current amplitude detected.

The control system includes means for automatically operating the measuring system to make periodic measurements of the sulfate content, and for adding a selected amount of sulfate to the solution when a measurement is below the selected value. Also included is a specific gravity unit automatically operated at prescribed intervals to measure the chromium trioxide content of the solution, and for adding a selected amount of chromium trioxide to the solution when a measurement is below a prescribed value.

33 Claims, 8 Drawing Figures

INVENTOR
WILLIAM H. PLUMPE, JR.
BY
Rogers, Ezell, Eilers & Robbins
ATTORNEYS

SYSTEM FOR AUTOMATICALLY MEASURING AND CONTROLLING THE SULFATE CONTENT OF A CHROMIUM PLATING SOLUTION

This is a continuation, of application Ser. No. 212,198 filed Dec. 27, 1971, now abandoned.

BACKGROUND OF THE INVENTION

The standard chromium plating solution includes chromium trioxide and sulfuric acid dissolved in water. For example, a standard solution might include 33 ounces of chromium trioxide and 0.33 ounces of sulfuric acid per gallon of solution. While this is a common concentration, the chromium trioxide may vary from 20 to 50 ounces per gallon although, in most cases, the 100 to 1 ratio of chromium trioxide to sulfuric acid is maintained. This is called a 1% solution. Whether this or some other percentage is desired for a particular application, the percentage is critical to insure proper and effective plating and must therefore be known. For this reason, certain tests were developed in the prior art to make this measurement.

Perhaps the most common sulfate test, at present, consists of adding barium chloride to a measured amount of plating solution. The sulfate is precipitated out as barium sulfate. The solution containing barium chloride is placed in a test tube and centrifuged to pull the barium sulfate into a small diameter extension in the bottom of the tube. The level of the barium sulfate is read on a scale printed on the tube. Each measurement requires at least two centrifuging operations and several measurements are required to insure accurate results. The test requires about 15 to 20 minutes to perform and its success, of course, depends on the performer's skill.

Another prior art means for making percent sulfate measurements is a device called an LPW sulfometer which is quite old and no longer used, presumably because it was awkward and unreliable. The device includes a couple of electrodes, one of brass and the other of lead, connected through a rheostat to a DC power supply. An ammeter is also connected in the circuit to measure the current through the electrodes. To measure the sulfate content, the brass and lead electrodes are immersed in the solution, and the operator then varies the rheostat gradually at a prescribed rate and as steadily as he can to gradually increase the voltage on the electrodes. As will be further explained later in this application, a point is reached where the current through the electrodes begins to decrease as the voltage increases. This is a peculiar characteristic of the plating solution. The magnitude of this current peak is directly proportional to the sulfate content of the solution. Hence the operator, watching the ammeter mentally notes where the maximum reading occurs and with the meter graduated in percent sulfate, reads the sulfate content of the solution.

There were several problems with the LPW sulfometer device. For one thing, the brass electrode was attacked by the solution each time the test was made and had to be either replaced or repolished after each test. Also the lead electrode had to be cleaned after each test. Another problem was that the electrodes were improperly configured so that the measurements were often inconsistent and unreliable. Additionally, the accuracy of the results depended on the skill of the operator to manually vary a rheosotat at a prescribed rate, which is virtually impossible to do. For this reason, the LPW sulfometer device is generally not used today.

Obviously, neither of these prior art methods or devices offers a completely automatic system for measuring the sulfate content of a chrome plating solution; and, hence, there is no system presently available for automatically controlling the solution. Therefore, it is a primary object of this invention to provide a completely automatic device for making these measurements accurately and in only a few seconds, which device uses components which are not attacked by the solution and therefore permanently re-usable, and which can be used for automatically controlling the solution.

SUMMARY OF THE INVENTION

The measuring apparatus of this invention includes a self-contained unit which houses the power source, circuitry and meter components of this invention, and further includes a probe having two electrodes, one of which, the cathode, is gold and the other, the anode, is platinum, which electrodes are electrically connected by a suitable conductor to the circuitry of the unit. The electrode's design is important in producing accurate measurements. The design details of the probe will be hereinafter described in more detail; but generally the anode must be relatively large compared to the cathode, and the configurations of each are critical.

The circuitry of the unit includes an integrator network which applies a linearly increasing voltage to the electrodes at a prescribed rate, and further includes a means for measuring the current through the electrodes. A track and hold network permanently records on the meter a reading proportional to the peak current through the electrodes as the voltage varies across them. An alarm circuit is also provided for signaling when the reading is complete. With the meter graduated in percent sulfate, the sulfate content can be read directly on the meter with the entire procedure taking only a few seconds. The unit is completely automatic, providing extremely accurate measurements. Means are also provided for compensating the readings for variances in solution temperature.

The system of this invention for automatically controlling the solution includes a source of sulfuric acid which can be made to flow into the plating solution through a solenoid control valve. A timer automatically triggers the measuring unit of this invention to make periodic readings of the sulfate content of the solution. Means are also provided responsive to the readings to actuate the solenoid valve for a prescribed length of time to add a selected amount of sulfuric acid to the solution when the reading is below a prescribed level. The control system might also include means for controlling the other compounds such as chromium trioxide and water by means commonly known in the art.

These and other features of the invention will become obvious in referring to the drawings and detailed description to follow.

DETAILED DESCRIPTION OF THE PREFERRED EMBODIMENT

Before describing the apparatus of the invention, it will be helpful to understand the basic principle on which this invention operates. If two appropriate electrodes are immersed in a standard chrome plating solution and a voltage slowly increasing up to about 4 volts is applied to the electrodes, the current through the electrodes will be generally as shown by the current-voltage plot of FIG. 1. The curve 20 has two ranges 21 and 22 where the current decreases as voltage increases instead of the usual rise of current with increasing voltage. The ion in the chrome plating solution associated with the first negative resistance zone 21 has not been identified, although it is possible there may be some relation to the chromium content, but is probably not accurate enough to be useful; however, the second, larger, zone 22 is very useful for it is dependent on the sulfate content, and the amplitude of the peak 23 preceding the negative zone 22 is basically quite linear with variations in sulfate concentration. It is this linear relationship between the amplitude of the peak 23 and the sulfate content of the solution that is made use of by this invention.

Because this linear relationship exists only where the temperature and the chromium trioxide content of the solution are constant, the measurements must be compensated for variations in temperature and chromium trioxide concentration. However, because the effects of these variations are easily and accurately predictable, the appropriate compensation in the measurement can be made very simply, as will be hereinafter described.

First, the operation of the unit, including its circuitry, will be explained, followed by a description of the probe portion of the unit. Finally, it will be explained how the unit is used in a control system for automatically controlling solution concentrations.

Figures 1, 2:
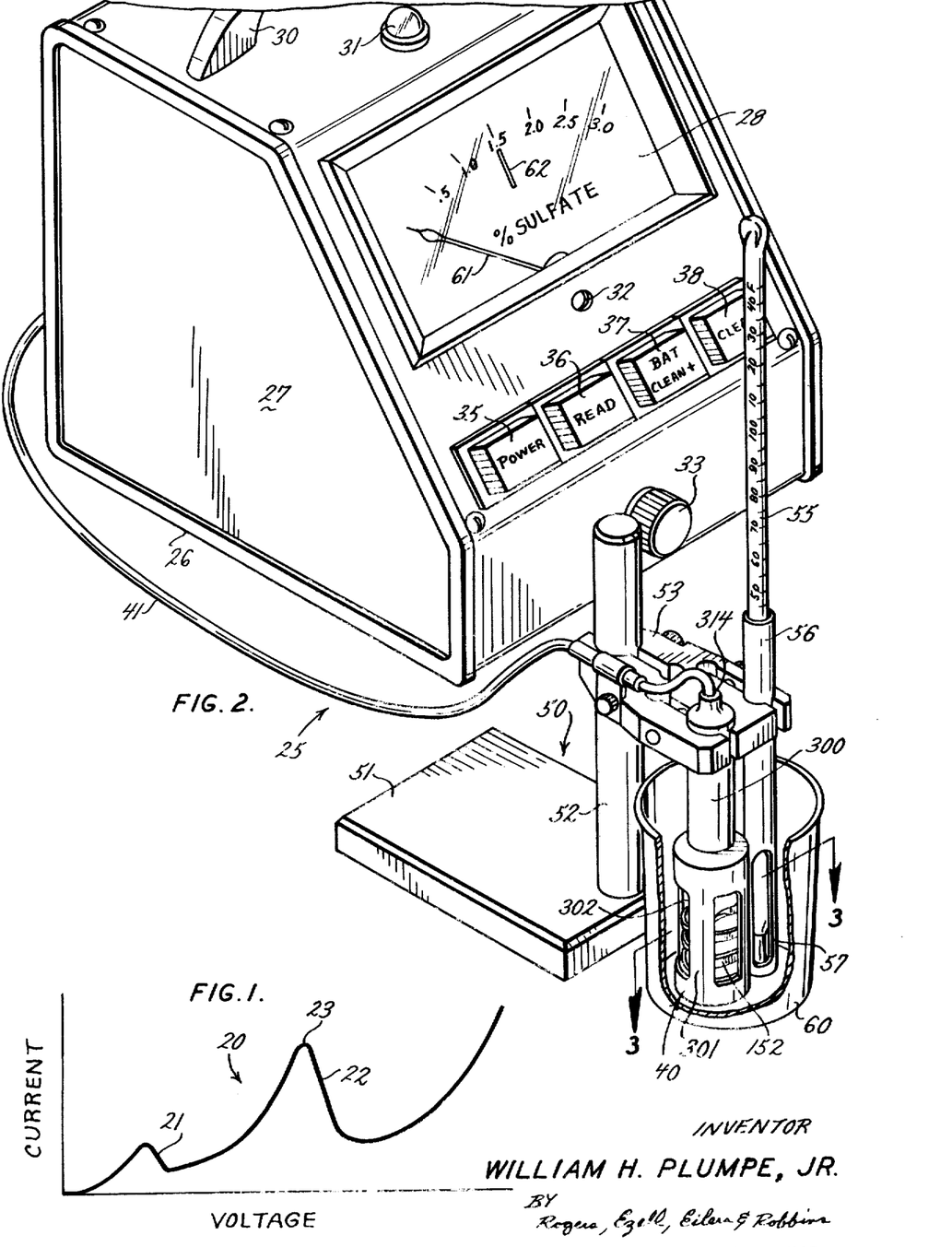
FIG. 1 is a voltage-current curve used in explaining the basic principle of the invention.
FIG. 2 is an isometric view of the self-contained reading unit and probe of this invention.

Referring to FIG. 2, there is generally shown the sulfate content measuring apparatus 25 of this invention which includes a self-contained unit 26 having a casing 27 which houses a meter 28 of a suitable type commonly known in the art, graduated in percent sulfate. Also in the unit 26 is a power supply (not shown) for the unit which is preferably a battery supply for portability and convenience, and the electronic circuitry of FIGS. 6 and 7. The unit 26 also includes a suitable handle 30, a signal light 31 for signaling when the power is on, a zero set control 32 used for zeroing the meter 28, a calibration control for calibratine the meter 28, and a plurality of buttons 35, 36, 37 and 38 which are the power, read, bat-clean + and clean − buttons, respectively, which buttons, when pressed, close switches which place the unit in various operating modes, as will be explained.

A probe 40 of a novel design to be hereinafter described, includes two electrodes, a cathode, preferably of gold, and an anode, preferably of platinum, which are electrically connected by conductors housed in a cable 41, through a suitable plug and receptacle (not shown) in the wall of the housing 27, to the electrical circuitry of the unit. The probe 40 is supported on a stand 50 having a base 51, a vertical support 52 and an adjustable mounting bracket 53. One end of the mounting bracket 53 is adjustably mounted on the support 52. The probe 40 is mounted at the other end of the bracket 53. A thermometer 55 used for measuring the solution temperature, which temperature measurement is used to compensate the sulfate reading for temperature variations, is supported within a cylindrical tube 56 mounted to the mounting bracket 53. The lower end of the tube 56 has openings 57 through which the chromium plating solution contacts the bulb of the thermometer. A sufficient portion of the thermometer extends above the top of the tube 56 so that the thermometer can be read. The probe and bottom part of the thermometer are shown placed in a suitable receptacle 60 for holding a sample of the solution to be tested.

Generally, the unit is operated by first pressing the button 37. If the pointer 61 passes the mark 62 of the meter 28, the batteries are good. If not, the batteries should be replaced. After releasing the button 37, the power button 35 is depressed and released. This energizes the unit by supplying bias voltage to various circuit components. The bulb 31 will light to indicate that the power is on. With the power on, the read button 36 is depressed and held depressed for approximately two seconds to reset the circuits. The meter 28 should read zero, as shown in FIG. 2, after the button 36 is released. If it does not, the zero adjust 32 should be adjusted to zero the meter. Once adjusted, the zero setting should hold for weeks and need only occasional adjustment. After the meter is zeroed, the unit is turned off by depressing the power button 35. Before testing an unknown solution, the meter 28 must be calibrated to read 1% in a standard solution at or near the concentrations to be measured, such as, for example, a solution of 33 ounces of chromium trioxide and 0.33 ounces of sulfuric acid per gallon of solution at 75° F where standard solution concentrations of about 33 ounces per gallon are to be measured. Sufficient standard solution is placed in the receptable 60 to cover the electrodes of the probe. The power button 35 is again depressed to turn on the unit and read button 36 depressed to initiate the measurement. As soon as the button 36 is depressed, the indicator 61 will slowly rise to a peak value and stop, whereupon an audible "beep" will signal that the reading is completed. If the meter does not read 1%, the calibration control 33 should be adjusted so that it does. With the meter calibrated, the power should be turned off, the probe removed from the solution and rinsed thoroughly with water. The unit is now calibrated to read an unknown solution by placing the probe in a sample of the unknown solution, turning the power on, and depressing the read button 36. Again the "beep" will signal completion of the reading and the percent sulfate in the unknown solution is read directly on the meter.

With proper use, the electrodes should not become plated, but should this inadvertently occur, the buttons 37 and 38 may be alternately depressed to produce small positive and negative currents respectively through the electrodes, when the power is on and the probe in solution, to deplate the electrodes.

There are two factors that introduce error into the percent sulfate readings. One is temperature change in the solution, and the other is the chromium trioxide content of the solution.

The readings of the measuring unit 25 have a temperature co-efficient of 1% of the reading at 75° F. per ° F. The instrument should be calibrated to read 1% on the standard solution at 75° F. To compensate the meter reading for temperature change, the temperature of the unknown solution is read on the thermometer 55 at the same time the sulfate content is measured. Suppose, for example, that the temperature reading is 85°. In this case, the temperature of the unknown solution is 10° higher than the solution at which the meter was calibrated; therefore, the reading is 10% too high, 1% for each 1° F. variation from 75°. Hence, the corrected reading is obtained by multiplying the measured reading by a factor of 100/110. The temperature compensation described is linear from about 50° F. to at least 120° F.

If the chromium trioxide concentration varies from the normal 33 ounces per gallon, another correction must be made. If a standard solution has 3.3 ounces per gallon of chromium trioxide added, the percentage sulfate reading should drop 10% because the chromium trioxide concentration has increased 10%. However, the reading will only drop 5%. Therefore, another correction must be made. To make the correction, the percentage variation of chromium trioxide is calculated and a correction of half this amount is applied to the sulfate reading. For example, suppose the chromium trioxide value obtained from a specific gravity measurement (commonly known in the art) is 34 ounces per gallon and the measured sulfate reading is 1.10%. A 1 ounce per gallon chromium trioxide change amounts to 3% so the sulfate reading must be multiplied by a factor of 100/101.5 to get the corrected reading. If the chromium trioxide reading is high, the sulfate reading must be reduced and vice versa. Of course, the error introduced by changes in chromium trioxide concentration can be eliminated by simply holding the chromium trioxide concentration at 33 ounces per gallon.

Having described the operation generally, the detailed operation will be described by referring to the schematic of FIG. 6.

When the power button 35 is depressed and released, a switch 65 is closed to supply positive 15 volts through a conductor 66 and a conductor 67 to energize an integrator 68. The voltage on the conductor 66 is also fed through a conductor 69 and a conductor 70 to energize an amplifier 71. The voltage on the conductor 69 is also fed through a conductor 72 and a conductor 73 to the collector of a transistor 74. The voltage on the conductor 72 is also fed through a conductor 75, a conductor 76, a resistor 77 and a conductor 78 to the base of a transistor 79. The voltage on the conductor 75 is also fed through a conductor 80 and a resistor 81 to the collector of the transistor 79. The voltage on the conductor 80 is also fed through a conductor 83, a conductor 84, a conductor 85 and a conductor 86 to one side of a switch 87. The voltage on the conductor 85 is also fed through a conductor 89 to energize an amplifier 90.

Also, when the switch 65 is closed, a minus 15 volts is fed through a conductor 95 to energize the integrator 68, and a conductor 97, resistor 98 and a conductor 99 to the inverting input of the integrator 68. The negative 15 volts is also fed through a conductor 102 to one side of a capacitor 103, and a conductor 104, and a conductor 105 to energize the amplifier 90. The voltage on the conductor 104 is also fed through a conductor 107, a conductor 110, a conductor 111, and a resistor 112, to the emitter of the transistor 79. The voltage on the conductor 111 is also fed through a resistor 113 to the emitter of the transistor 74. The voltage on the conductor 110 is also fed through a conductor 115 and a conductor 117 to the emitter of a transistor 119. The voltage on the conductor 115 is also fed through a conductor 121 and a conductor 123 to the emitter of a transistor 125. The voltage on the conductor 121 is also fed through a conductor 127 to the emitter of a transistor 129. In this manner, the plus and minus 15 volt bias voltages are applied to the appropriate components of the circuit.

With the power to the circuit on, a reading is made by depressing and releasing the read button 36. When the button 36 is depressed and released, a switch 140 is momentarily closed to apply a negative 1.5 volts from a battery 141 to the inverting input of the integrator 68 and across a capacitor 142 and a diode 143. Closing the switch 140 also discharges a capacitor 144 to initiate operation of the integrator 68 as will be explained. With the non-inverting input of the integrator 68 connected through a conductor 145 to ground, the output voltage of the integrator 68 will begin rising at a constant rate from 1.5 volts. In this embodiment the integrator is of a type to cause the output voltage to rise about 2½ volts per minute. It is important that the output start at about 1.5 volts in order to miss the first peak shown in FIG. 1. Otherwise the circuit will follow the first peak and give an erroneous reading. The output voltage from the integrator 68 is fed through a conductor 150, a conductor 151, and a couple of switches to the anode 152 of the probe 40. From the anode 152 the integrator output is fed through the chromium plating solution into which the probe 40 is immersed, a cathode 154 of the probe 40, a conductor 155, a conductor 156 and a resistor 157 to ground.

The voltage across the resistor 157 is proportional to the current through the solution and tends to sharpen the peak 23 of FIG. 1 by increasing the negative slope 22. This is so because, as the voltage increases across the electrodes 152 and 154, and the resistance of the solution increases in the range of the slope 22, the voltage across the electrodes increases rapidly which, in turn, decreases rapidly the voltage across the resistor 157. Hence, the voltage across the resistor 157 peaks and then drops off very quickly. This is important in order to get precise readings.

The voltage at the resistor 157, which is proportional to the current through the solution and therefore the magnitude of the peak 23 of FIG. 1, which in turn is proportional to the sulfate content of the solution, is fed through a conductor 160 to the non-inverting input of the amplifier 71, a 1:1 voltage follower, causing its output to follow the voltage at the non-inverting input. This output voltage is fed through a conductor 161, a conductor 162 and a resistor 163 to the gate of a junction field effect transistor (NJFET) 165. The transistor 165 has a source 166 and a drain 167 and operates such that when the gate is positive with respect to the source and drain, all its junctions are connected, and when the gate is negative with respect to the source and drain, all its junctions are disconnected. The source 166 is connected through a conductor 168, a conductor 169 and a conductor 170 to the inverting input of the amplifier 71. Hence, with the amplifier 71's non-inverting input following the voltage across the resistor 157, its inverting input connected to the source of the transistor 165, and its output connected through the resistor 163 to the gate of the transistor 165, the gate is positive with respect to the source and drain causing the transistor 165 to conduct from source to drain. Therefore, the voltage at the inverting input of the amplifier 71, which is following the voltage at its non-inverting input is fed through the conductors 170, 169, and 168, the source and drain junction of the transistor 165, and a resistor 173 to charge the capacitor 144. The capacitor 144 is of a low leakage type to hold the charge.

The voltage on the capacitor 144 is fed through a conductor 176 and a conductor 178 to the non-inverting input of the amplifier 90, which is also a 1:1 voltage follower, and is of a type designed with a very high input impedence of, for example, $10^{11}$ ohms so that the voltage on the capacitor 144 can be read without discharging it rapidly. The output voltage from the amplifier 90 which follows the voltage at the non-inverting input and is therefore increasing with the voltage on the capacitor 144, is fed through a conductor 180, a resistor 181, a diode 182, a conductor 183, and the conductors 169 and 170 to the inverting input of the amplifier 71.

The output voltage from the amplifier 90 is also fed through a conductor 190, a resistor 191, a variable resistor 192 and a switch to the meter 28, causing the meter 28 to follow the voltage on the capacitor 144. The variable resistor 192 is varied by operating the calibration control 33 for purposes of calibrating the meter 28 as heretofore described.

With the voltage across the resistor 157, appearing through the amplifier 71 transistor 165, and amplifier 90, at the inverting input of the amplifier 71, as soon as the voltage across the resistor 157 begins to drop which is just after it reaches the peak 23 of FIG. 1, the non-inverting input of the amplifier 71 will become negative with respect to its inverting input causing its output to be negative with respect to its inverting input in turn causing the gate of the transistor 165 to become negative with respect to its source and drain. This effectively opens the source and drain junction isolating the capacitor 144 from the rest of the circuit except, of course, for the meter circuit. Hence, the voltage stored on the capacitor 144 is a peak voltage proportional to the current through the solution, which voltage is fed through the amplifier 90 to the meter 28. With the meter scale graduated in percent sulfate the indicator 61 of the meter is made to read directly the sulfate content of the solution.

In the meantime, the integrator 68 is still operating to produce an increasing voltage at its output. To turn off the integrator 68, the output voltage from the amplifier 71 is fed through the conductor 161 and a resistor 200 to the base of the transistor 74. The collector of the transistor 74 is connected through conductors 73, 72, 69, 66 and the switch 65 to the positive 15 volt source as heretofore described. The emitter of the transistor 74 is connected through the resistor 113 and conductors 111, 110, 107, 104, 102, and the switch 65 to the negative 15 volt source. The emitter of the transistor 74 is also connected through a Zener diode 201 and the resistor 202 to the base of the transistor 79. A diode 203 and a capacitor 204 are connected between the transistors 74 and 79 as shown in FIG. 6. A diode 205 is connected as shown between the emitter of the transistor 79 and ground.

As long as the voltage at the output of the amplifier 71 is increasing, the transistor 74 conducts causing the transistor 79 to conduct holding the collector voltage of the transistor 79 at a low enough value so as to not affect the operation of the integrator 68. But as soon as the amplifier 71 swings negative, the transistor 74 is cut off which in turn cuts off the transistor 79 bringing its collector voltage up to 15 volts which voltage is fed through a conductor 210, a diode 211, a conductor 212, and the conductor 99 to the inverting input of the integrator 68 causing the output of the integrator 68 to swing negative until the diode 143 conducts which is when the voltage at the output of the integrator 68 is about minus 400 millivolts, the forward breakover voltage of the diode. The output of the integrator 68 then holds this value. This small negative voltage at the output of the integrator 68 is desirable for it produces a small negative current through the electrodes to remove any foreign molecules that may have adhered to the cathode.

Therefore, as can be seen, the integrator 68 will operate to produce at its output a positive sloping ramp function which if left to operate long enough, perhaps six minutes, will reach 15 volts unless the voltage across the resistor 157 is less than the voltage on the capacitor 144, in which case the transistor 79 stops conducting to apply a positive 15 volts to the inverting input of the integrator 68 to reverse its output. This explains how the switch 140 operates to initiate operation of the integrator 68. After a reading, the capacitor 144 is at a higher potential then the resistor 157 to hold the integrator output at about minus 400 mv as heretofore described. When the switch 140 is momentarily closed by depressing and releasing the read button 36, the capacitor 144 is discharged through a resistor 214, and a small positive voltage applied across the resistor 157 from the battery 141 with the electrodes in solution. This makes the voltage across the resistor 157 greater than the voltage on the capacitor 144 to initiate operation of the integrator 68.

With the circuit as thus far described, if the power is turned on with the electrodes out of solution, the integrator output will increase to 15 volts if there is no charge on the capacitor 144, since there is no decreasing current characteristic to make the voltage on the resistor 157 negative with respect to the voltage on the capacitor 144. If the electrodes are immersed in the solution with positive 15 volts on the anode 152, the cathode will immediately become badly plated and erroneous readings will result. The circuit, therefore, includes a feature to hold the integrator off before the read button is depressed. When the power switch 65 is closed, a capacitor 215 couples a pulse from the conductor 89 through the conductor 176 to put a small positive charge on the capacitor 144. With the electrodes out of solution the voltage on the resistor 157 is zero and therefore negative with respect to the voltage on the capacitor 144 to hold the integrator output at about minus 400 mv as heretofore described. If the electrodes are then placed in the solution after the power is on, the small negative current tends to deplate the cathode which is desirable.

Because the current through the electrodes is subject to fluctuations from bubbles and other noise sources, the resistor 163 insures that the charge on the capacitor 144 reflects the average current through the solution rather than the instantaneous noise peak. For the same reason, the network including the Zener diode 201, resistor 202, diode 203, and capacitor 204 is included between the transistors 74 and 79 to prevent the transistor 79 from triggering on noise. Various other resistors and capacitors are used in the circuit for the purposes of overload protection to prevent damaging the various amplifier inputs and transistor bases, to improve circuit stability or to prevent malfunction from noise as commonly known in the art.

The network about to be described is not necessary to make readings, but operates an alarm to give a short "beep" when the integrator output drops, indicating a completed reading. The output of the integrator 68 is fed through the conductor 150 and a conductor 217 to the base of a transistor 219. The emitter of the transistor 219 is connected by a conductor 221 to ground and through a resistor 223 to the collector of the transistor 129. The collector of the transistor 219 is connected through a resistor 225 to the base of the transistor 129. The collector of the transistor 129 is connected through a capacitor 231 to the base of the transistor 125. The base of the transistor 125 is connected through a resistor 232 to the conductor 84, and a capacitor 233 to the collector of the transistor 119 which in turn is connected to an alarm 235. The collector of the transistor 125 is connected through a resistor 236 to the conductor 85. The other side of the alarm 235 is connected to one side of the switch 87, the other side of which is connected through the conductors 86, 85, 84, 83, 80, 75, 72, 69, and 66, and the switch 65 to the positive 15 volt supply. The emitters of the transistors 129, 125, and 119 are connected together by conductors 127 and 121, and to the negative 15 volt supply by the conductors 115, 110, 107, 104, 102, and the switch 65.

When the output voltage from the integrator 68 becomes negative, which is when the integrator is shut off after the peak 23 is reached, this negative voltage, which is fed through the conductors 150 and 217 to the base of the transistor 219, causes the transistor 219 to conduct which in turn causes the transistor 129 to conduct producing an AC pulse coupled through the capacitor 231 to the base of the transistor 125. This AC pulse turns on the transistor 125 which turns on the transistor 119. With the transistor 119 turned on and the switch 87 closed, the alarm 235 is across the plus and minus 15 volt supplies causing the alarm to operate for the duration of a feedback pulse through the capacitor 233. At the end of the feedback pulse the transistors 125 and 119 will turn off causing the alarm 235 to turn off. Hence, the alarm operates to produce a short "beep" to indicate that the reading is completed.

The details of the battery check, clean + and clean − circuits will now be described.

When the power to the circuit is off, the switch 65 connects positive 15 volts to a switch terminal 240, and negative 15 volts to a switch terminal 241. When the bat-clean + button 37 is depressed, it closes a double-pole, double-throw switch 243 shown in the diagram in its open position. With the switch 65 open, and the switch 243 closed, positive 15 volts is fed through the switch 65, a conductor 245, a resistor 246, the switch 243, and a conductor 247 to the anode 152 producing a positive current through the electrodes. The open contact of the switch 243 is connected by a conductor 249 to the wiper arm of a switch 251 shown in the diagram in its open position. The closed contact of the switch 251 is connected by a conductor 253, and a resistor 255, to the contact 241 of the switch 65. When the clean − button 38 is depressed, it closes the switch 251, and with the switches 65 and 243 in their open positions, negative 15 volts is fed through the switch 65, the resistor 255, and the switches 251 and 243 to the anode 152 to produce a negative current through the electrodes. By alternately depressing and releasing the buttons 37 and 38, positive and negative currents are produced through the electrodes to deplate the cathode should this become necessary.

When the button 37 is depressed to close the switch 243, and the power switch 65 is in its off position, positive 15 volts is fed through the switch 65, the conductor 245, a resistor 261, and the switch 243 to the meter 28 to cause the meter to read a value proportional to the voltage of the positive power supply battery to check the positive battery supply. Because there is a greater load on the positive supply than the negative supply, a meter indication that the positive supply is good means the negative supply is also good.

Figures 6, 7:
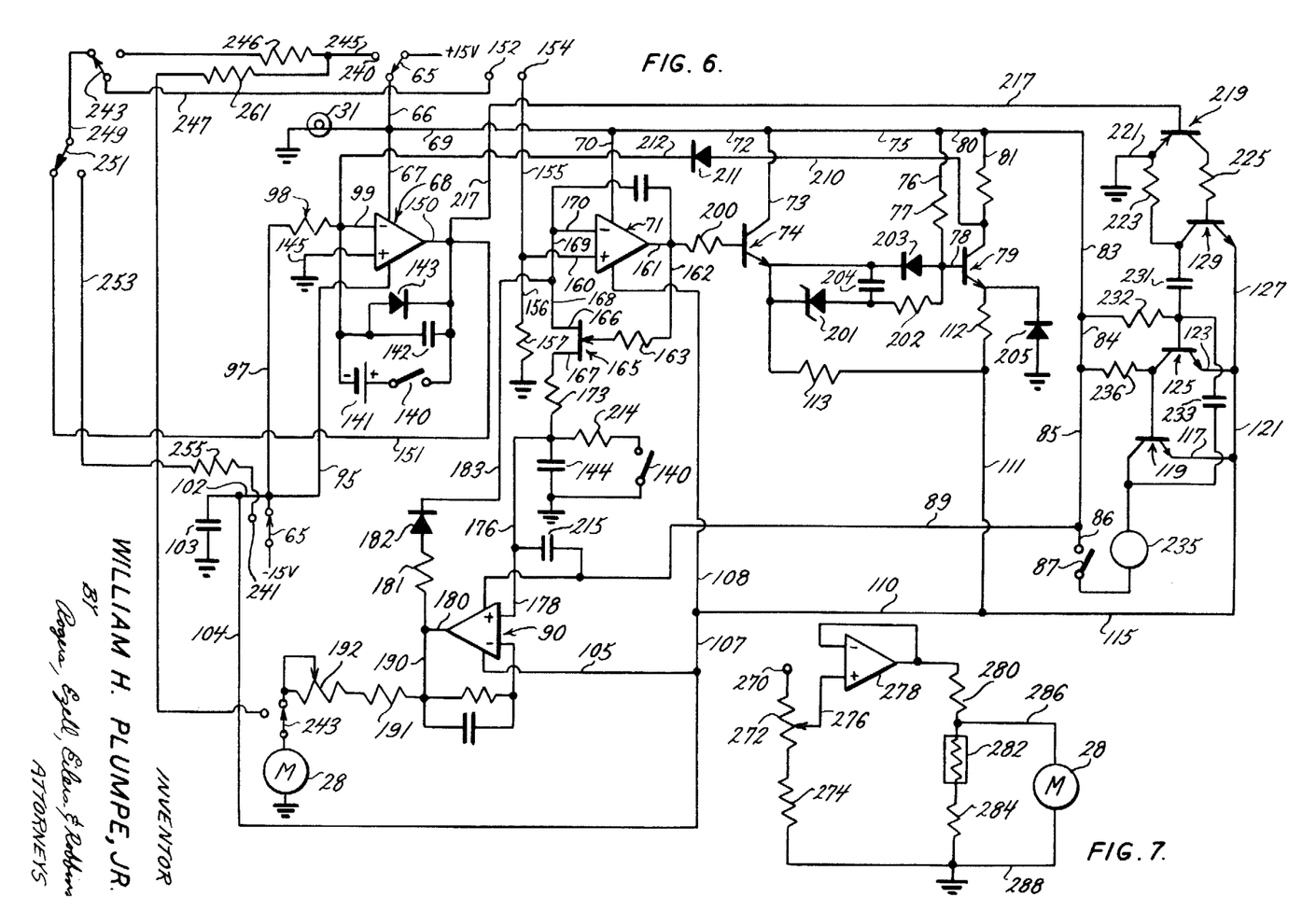
FIG. 6 is a schematic drawing of the basic electronic circuitry of the measuring unit of this invention.
FIG. 7 is a schematic drawing of a temperature compensation circuit of this invention.

In FIG. 7, there is shown a circuit for automatically compensating the meter readings for changes in temperature of the solution without the need of the thermometer 55 and the readings and calculations associated therewith. The circuit of FIG. 7 is used in place of the resistors 191 and 192 and the meter 28 as shown in FIG. 6 and has an input 270 which would be connected to the output of the amplifier 90. A variable resistor 272, providing a calibration adjust for the meter 28, and a resistor 274 are in series between the input 270 and ground. The wiper arm of the variable resistor 272 is connected by a conductor 276 to the non-inverting input of an isolation amplifier 278. A resistor 280, a thermistor 282, and a resistor 284 are connected in series as shown between the output of the amplifier 278 and ground. The meter 28 is connected by leads 286 and 288 across the thermistor 282 and resistor 284. The amplifier 278 is used to isolate the effects of resistance change at its input caused by varying the variable resistor 272 and resistance change at its output caused by temperature change of the thermistor 282. The thermistor 282 is physically attached to the probe 40 so that it is immersed in the solution when a measurement is made.

In operation, the meter 28 is calibrated as heretofore described by adjusting the variable resistor 272 by means of the central knob 33. When measuring the sulfate content of an unknown solution, the thermistor 282 will attain a resistance value in accordance with the temperature of the solution. As the temperature increases, its resistance decreases to reduce current to the meter 28, and as the temperature decreases, its resistance increases to supply more current to the meter 28, in this way compensating the meter reading for variations in temperature. The values of the resistors 280 and 284 and the the thermistor 282 are selected so that the meter reading is correctly compensated at the solution temperature, i.e. so that a 1% change is reading per 1°F. variation from 75°F. is produced.

Referring to FIGS. 2 through 5, the probe 40 of this invention includes an upper solid cylindrical portion 300 and a lower hollow cylindrical poriton 301 of a larger diameter than the portion 300 and having elongated openings 302 therein to form a housing for the electrodes. The portions 300 and 301 are of plexiglass of other suitable insulating material which is not attacked by the chromium plating solution. A glass tube 305 extends from within the portion 300 part way into the portion 301 and has sealed therein a platinum ribbon 307 a length of which extends from the bottom of the tube 305 and is wound in a spiral 152 around the inner surface of the portion 301 to form the anode of the probe. The spiral 152 is bonded to the wall of the portion 301 along one side as at 309. A second glass tube 310 extends from within the portion 300 and terminates at its lower end in an L-shaped portion 311 near the bottom of the portion 310. A gold ribbon 312 is sealed within the length of the tube 310 and has a small portion 154 extending from the lower end of the tube to form the cathode of the probe.

Figures 3, 4, 5:
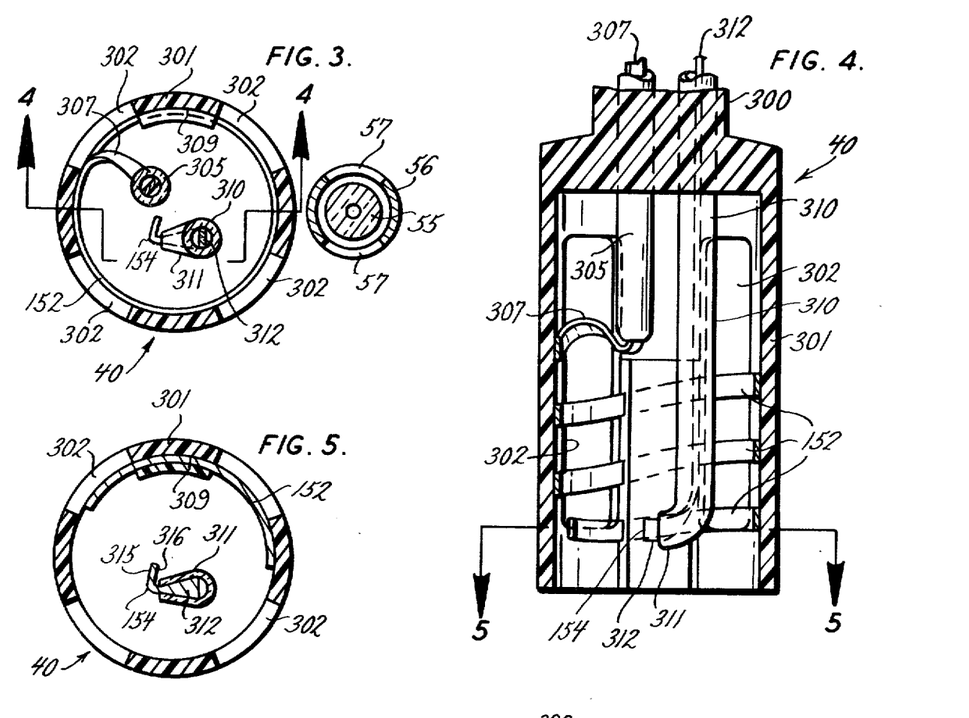
FIG. 3 is a view in section taken along the line 3—3 of FIG. 2.
FIG. 4 is a view in section taken along the line 4—4 of FIG. 3.
FIG. 5 is a view in section taken along the line 5—5 of FIG. 4.

The cable 41 extends through an aperture 314 in the top of the probe and includes one electrical conductor connected to the top end of the anode ribbon 307 and another connected to the top end of the cathode ribbon 312. The entire area within the upper portion 300 of the probe is sealed with an appropriate sealing compound to prevent solution, or water used to clean the probe, from shorting the electrodes.

The choice of platinum and gold for the anode and cathode respectively is important, for while other combinations of metals will work, they are attacked by the solution and have to be replaced, some of them after having been used only once, or do not give as accurate readings. On the other hand, the gold and platinum electrodes can be used indefinitely with proper care, and are very accurate.

The design of the probe, specifically the design of the electrodes, is also important. Without proper electrode design, accurate readings cannot be obtained consistently. There appear to be two primary factors affecting cathode geometry. The first is that a dark brown layer (possibly trivalent chrome, although this is not known for sure) begins to form around the cathode, sometime between the first and second current peaks of FIG. 1. This coating introduces a resistance in the system that makes the higher concentration readings lower than their true values. Since this coating tends to flow downward along the cathode, a long vertical cathode will form a thicker coating on its lower portion, increasing the error. The second factor is the pattern of the current radiating out into solution. The active area seems to be a layer in the solution outside of the brown layer and very near the cathode. If the cathode is a point, this second layer will have a much larger area than the cathode or the brown layer and consequently will have a lower current density, whereas a flat plate cathode configuration will result in nearly equal current densities in all areas except around the edges of the plate. Of course, if the plate has a larger vertical dimension, the first form of interference will occur, namely, the downward flow of the brown layer. For these reasons, a vertical wire or a point make very poor cathode configurations, while a thin plate with a nearly flat surface which is relatively short in the vertical direction makes a very good one.

The cathode design of this embodiment is of the latter type, and therefore produces very accurate and consistent readings. The cathode ribbon 154 is relatively thin with nearly flat surfaces 315 and 316. It is oriented with its width vertically and approximately centered within the spiral anode 152. The width of the cathode 154, which is its vertical dimension, is relatively narrow to eliminate the problem caused by the buildup of the brown coating on its walls. As an example, in this described embodiment the dimensions of the cathode 154 are 0.010 inches thick, 0.090 inches wide, and 0.125 inches long. With the cathode ribbon being very thin, the current density at the surfaces of the cathode is about the same as at the second layer previously discussed to substantially eliminate the problem caused by the difference in current densities between the cathode and second layer.

Two other features of the probe configuration are important: electrode spacing and size. The spacing between the surfaces of the cathode 154 and the nearest inner surface of the spiral anode 152 must be sufficient to allow space for this layer phenomenon (or whatever else occurs between the electrodes) to take place. This spacing should therefore be at least 3/16 of an inch and approximately no more than 3 inches. Generally, the object is to minimize the effect of the anode by making the current density at the anode much less than at the cathode. This is done by making the anode large compared to the cathode and spacing them a sufficient distance apart. If the anode is too small, the effects of solution temperature change become much greater than the 1% per °F. variation from 75°F. previously described, and the correction factor becomes unmanageable. The minimum size ratio of anode to cathode can be determined empirically and should be high enough that the temperature correction factor of 1% per ° F. variation from 75°F. exists.

In this respect, the anode does not necessarily have to be a spiral. It could, for example, be a solid cylinder. However, a spiral works just as well, and with the use of platinum is far less expensive. In this embodiment the anode is 3/32 inches wide wound in a ¾ inch diameter spiral. The distance between the surface 315 of the cathode and the nearest inner surface of the anode is approximately ¼ inch.

If air bubbles accumulate on the cathode, it could affect the accuracy of the readings. Therefore, the cathode 154 is positioned near the bottom of the anode 152 so that any air bubbles formed on the anode that break loose will rise and miss the cathode.

Figure 8:
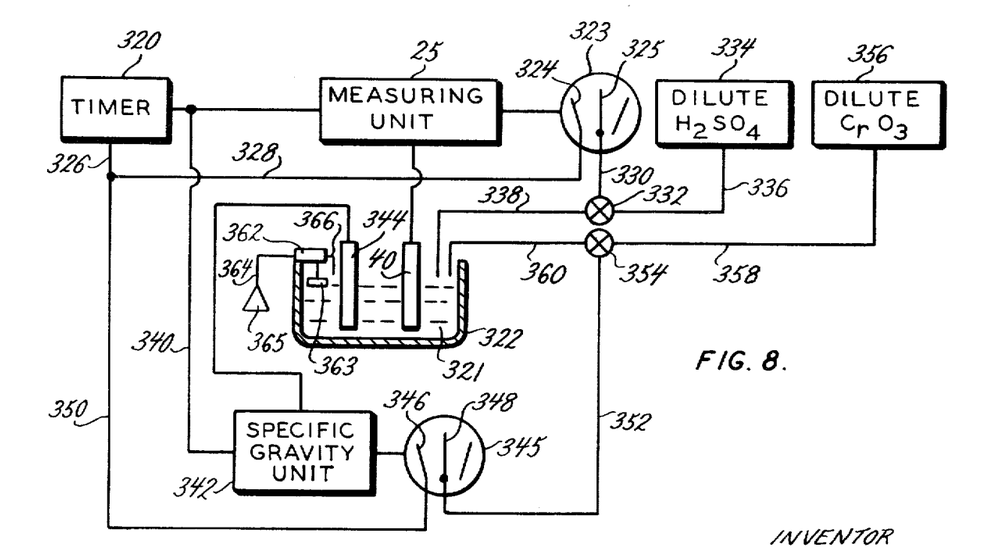
FIG. 8 is a block diagram illustrating an automatic control system of this invention.

In FIG. 8, there is shown a control system including the measuring instrument 25 heretofore described for automatically controlling the sulfate and chromium trioxide concentration of a chromium plating solution. The control system includes a timer 320 connected to the measuring unit 25 which includes the probe 40 of this invention. The electrodes of the probe 40 are immersed in the solution 321 to be controlled which solution is contained in a tank 322. The timer 320 automatically operates the read circuit of the unit 25 at intervals determined by the depletion rate of the particular plating tank ranging from perhaps every 15 minutes on a rapidly depleting system to several hours on a slow one. In other words, the timer 320 does automatically what the person operating the unit 25 does manually by pressing the read button 36. Each time the timer operates the read circuit of the measuring unit 25, a meter 323 registers a reading representing the sulfate content of the solution 321.

The meter 323 replaces the meter 28 and is of the type that closes a contact 324 when the reading falls below a preset value as indicated by an arm 325.

After the reading is completed, the timer 320 applies a voltage through a conductor 326 and a conductor 328 to the contact 324 for a prescribed length of time, perhaps 30 seconds. If the meter reading is below the limit set by the contact 324, the voltage on the contact 324 is fed through the arm 325 and a conductor 330 to open an adjustable solenoid valve 332. With the solenoid valve 332 open, a supply 334 of dilute sulfuric acid is fed through a conduit 336, the valve 332 and a conduit 338 into the tank 322. The valve 332 should be adjusted to dispense the correct amount of acid relative to the volume of the tank to return the solution to the desired concentration. This flow of sulfuric acid continues into the tank as long as the timer supplies the voltage to operate the valve 332. For example, if the timer is set to generate the voltage for 30 seconds, then the flow of sulfuric acid continues into the tank for 30 seconds. If after a reading is completed the arm 325 is not below the lower limit contact 324, indicating that the sulfate content of the solution is within tolerance, the solenoid valve 332 is not operated, and no sulfuric acid flows into the tank. Each time the timer 320 operates the read network of the measuring unit 25 to make a reading, this process if repeated until eventually the sulfate content is brought up to the desired amount. The timer 320 should be set so that the time interval between readings is long enough to allow any added acid to mix thoroughly in the tank.

A dilute solution of sulfuric acid is used because the volume of sulfuric acid would otherwise be too small to meter efficiently unless the tank was very large.

To complete the control system, a parallel system is used to control the chromium trioxide content of the solution. The timer 320, through a suitable conductor 340, operates a specific gravity unit 342 having a probe 344 immersed in the solution 321 to measure the chromium trioxide content of the solution and register this reading on a meter 345 similar to the meter 323. The meter 345 has a lower limit contact 346 and an arm 348. When the reading on the meter 345 is below the value set by the contact 346, the timer 320 applies a voltage, after the reading is completed, through the conductor 326, a conductor 350, the contact 346 and arm 348, and a conductor 352 to operate a second adjustable solenoid control valve 354, allowing a source 356 of dilute chromium trioxide to flow through a conduit 358, the control valve 354, and a conduit 360 into the tank 322. If the reading of the meter 345 is above the lower limit set by the contact 346, indicating that the solution is properly balanced, the valve 354 remains closed, and no chromium trioxide is added to the tank. As can be seen, a single timer 320 can be used to operate both systems.

The only other parameter that need be controlled is the level of the solution in the tank. This can be done by a simple float valve 362, commonly known in the art, having a float 363, a water inlet 364 connected to a water source 365, and a water outlet 366 from which water from the water source 365 enters the tank when the valve 362 is open. This, of course, is when the float 363 indicates the solution to be below a prescribed level.

Therefore, there has been described a system for automatically measuring and controlling the sulfate content of a chromium plating solution, and which measurements are made quickly and accurately without the need for replacing electrodes.

Various changes and modifications may be made within the scope of this invention as will be readily apparent to those skilled in the art. Such changes and modifications are within the scope and teaching of this invention as defined by the claims appended hereto.

What is claimed is:

1. A measuring device for measuring the sulfate content of a chromium plating solution where a relationship exists between the voltage applied to the electrodes immersed in the solution and the current through the electrodes such that as the voltage increases from a prescribed first value, the current between the electrodes increases to a peak and then decreases, the magnitude of the current peak being directly proportional to the sulfate content of the solution, the device comprising spaced electrodes for immersing in the solution, said electrodes including a cathode of thin metallic ribbon, the surface of the cathode being relatively flat and its width dimension being oriented vertically in the solution, and a metallic anode surrounding the cathode, the device further comprising, electrical circuit means electrically connected to the electrodes, means associated with the circuit means for automatically applying a smoothly increasing voltage across the electrodes, means associated with the circuit means for starting the smoothly increasing voltage at a voltage value lower than that which produces the peak current between the electrodes and for continuously increasing the voltage to at least the value producing said peak current, to produce a current variation in the solution between the electrodes that increases to a peak, means for detecting the current variation in the solution as the voltage varies across the electrodes, and means for registering the peak current.

2. The measuring device of claim 1 including, means for generating a signal the magnitude of which varies in proportion to the current variation through the electrodes, means for storing the signal magnitude proportional to the peak current through the electrodes, and means for recording the signal magnitude proportional to the peak current.

3. The measuring device of claim 2 wherein the recording means includes a meter calibrated in percent sulfate, and including means for applying the stored signal whose magnitude is proportional to the current peak to the meter to cause the meter to record the peak magnitude and thereby indicate the percent sulfate content of the solution.

4. The measuring device of claim 2 wherein the means for starting and increasing the smoothly increasing voltage further comprises means for increasing the voltage to past the value producing said peak current, and wherein the storing means includes a track and hold network, means responsive to the application of the smoothly increasing voltage across the electrodes to cause the track and hold network to track the signal the magnitude of which varies in proportion to the current variation through the electrodes, and means responsive to a decrease in current through the electrodes to cause the track and hold network to hold the peak value of the signal.

5. The measuring device of claim 1 wherein the means for starting and increasing the smoothly increasing voltage further comprises means for increasing the voltage to past the value producing said peak current, and further including means responsive to a decrease in current through the electrodes for producing a small reverse flow of current through the electrodes.

6. The device of claim 5 including electrical circuit means responsive to production of a reverse flow of current through the electrodes for signalling completion of the reading.

7. The measuring device of claim 1 including means for automatically compensating the readings for variations in solution temperature, which means includes a thermistor in the solution for sensing the solution temperature and means responsive to variations in the thermistor resistance caused by variations in solution temperature to compensate the readings.

8. The measuring device of claim 1 wherein the electrical circuit means further comprises means for automatically applying the smoothly increasing voltage across the electrodes at a rate of increase not greater than 5 volts per minute.

9. The measuring device of claim 1 wherein the surface area of the anode is sufficiently greater than the surface area of the cathode, and the anode and cathode are spaced a sufficient distance apart, that each 1° Fahrenheit variation in temperature from 75° F. of the solution being measured requires a measurement compensation of 1%.

10. The measuring device of claim 1 wherein the shortest distance between the anode and cathode is at least 3/16 inch.

11. The measuring device of claim 1 wherein the anode is a spiral ribbon surrounding the cathode.

12. The measuring device of claim 1 wherein the anode is platinum and the cathode is gold.

13. The measuring device of claim 1 wherein the cathode width is approximately no greater than 0.250 of an inch.

14. The measuring device of claim 1 wherein the cathode is gold and the anode is a spiral ribbon of platinum surrounding the cathode, the width of the cathode being approximately no greater than 0.250 of an inch.

15. The measuring device of claim 14 wherein the shortest distance between the anode and the cathode is at least 3/16 inch.

16. A measuring device for measuring the amount of a particular chemical in a solution where a relationship exists between the voltage applied to electrodes immersed in the solution and the current produced thereby through the electrodes, such that as the voltage varies in one direction at a prescribed rate, the current first varies in one direction, reaches a peak, and then varies in the reverse direction, the amplitude of the peak being proportional to the amount of the particular chemical in the solution, the device comprising a probe having spaced electrodes for immersing in the solution, said electrodes including a first electrode of thin, metallic ribbon, the surfaces of the first electrode being relatively flat and its width dimension being oriented vertically in the solution, and a metal second electrode surrounding the first electrode, the device further comprising electrical circuit means electrically connected to the electrodes, means associated with the electrical circuit means for automatically applying a smoothly varying voltage in the one direction across the electrodes, means associated with the circuit means for starting the smoothly varying voltage at a value before the current peak occurs and for continuously varying the voltage in the one direction to at least the value producing the peak current, to thereby produce the current peak in the solution and through the electrodes, means for detecting the current variation in the solution as the voltage varies across the electrodes, and means for registering the peak current.

17. The measuring device of claim 16 wherein the second electrode is a spiral ribbon surrounding the first electrode.

18. The measuring device of claim 17 wherein the second electrode is platinum and the first electrode is gold.

19. The measuring device of claim 18 wherein the means for starting and varying the smoothly varying voltage in one direction further comprises means for varying said voltage in said one direction to past the value producing said peak current, and further including means responsive to a variation in current in the opposite direction through the electrodes for producing a reverse flow of current through the electrodes.

20. A measuring device for measuring the sulfate content of a chromium plating solution comprising a probe having spaced electrodes for immersing in the solution, the electrodes including a cathode of thin, metallic ribbon, the surfaces of the cathode being relatively flat and its width dimension being oriented vertically in the solution, and a metallic anode surrounding the cathode, the measuring device further comprising electrical circuit means for automatically applying a smoothly increasing voltage across the electrodes to produce a current variation in the solution through the electrodes, and means for detecting the current variation in the solution as the voltage varies across the electrodes.

21. The measuring device of claim 20 wherein the surface area of the anode is sufficiently greater than the surface area of the cathode, and the anode and cathode are spaced a sufficient distance apart, that each one degree Fahrenheit variation in temperature from 75°F of the solution being measured requires a measurement compensation of 1%.

22. The measuring device of claim 20 wherein the shortest distance between the anode and cathode is at least 3/16 inch.

23. The measuring device of claim 20 wherein the anode is a spiral ribbon surrounding the cathode.

24. The measuring device of claim 20 wherein the anode is platinum and the cathode is gold.

25. The measuring device of claim 20 wherein the cathode width is approximately no greater than 0.250 of an inch.

26. The measuring device of claim 20 wherein the cathode is gold and the anode is a spiral ribbon of platinum surrounding the cathode, the width of the cathode being approximately no greater than 0.250 of an inch.

27. The measuring device of claim 26 wherein the shortest distance between the anode and cathode is at least 3/16 inch.

28. A measuring device for measuring the sulfate content of a chromium plating solution where a relationship exists between the voltage applied to the electrodes immersed in the solution and the current through the electrodes such that as the voltage increases from a prescribed first value, the current between the electrodes increases to a peak and then decreases, the magnitude of the current peak being directly proportional to the sulfate content of the solution, the device comprising spaced electrodes for immersing in the solution, electrical circuit means electrically connected to the electrodes, means associated with the circuit means for automatically applying a smoothly increasing voltage across the electrodes, means associated with the circuit means for starting the smoothly increasing voltage at a voltage value lower than that which produces the peak current between the electrodes and for continuously increasing the voltage to past the value producing said peak current, to produce a current variation in the solution between the electrodes that increases to a peak, means for detecting the current variation in the solution as the voltage varies across the electrodes, means for registering the peak current, and means responsive to a decrease in current through the electrodes for producing a reverse flow of current through the electrodes.

29. The measuring device of claim 28 wherein the electrodes include a cathode of thin, gold ribbon, the surfaces of the cathode being relatively flat and its width dimension being oriented vertically in the solution, its width dimension being approximately no greater than 0.250 of an inch, and an anode comprising a platinum spiral ribbon surrounding the cathode.

30. A measuring device for measuring the content of a chemical in solution comprising a probe having spaced electrodes for immersing in the solution, the electrodes including a first electrode of thin, metallic ribbon, the surfaces of said first electrode being relatively flat and its width dimension being oriented vertically in the solution, and a second metallic electrode surrounding said first electrode, the measuring device further comprising electrical circuit means for automatically applying a variable voltage across said first and second electrodes to produce a current variation in the solution through said first and second electrodes, and means for detecting the current variation in the solution as the voltage varies across said first and second electrodes.

31. The measuring device of claim 30 wherein said second electrode is a spiral ribbon surrounding said first electrode.

32. The measuring device of claim 31 wherein said second electrode is platinum and said first electrode is gold.

33. The measuring device of claim 32 wherein the width of said first electrode is approximately no greater than 0.250 of an inch.

* * * * *